United States Patent [19]

Perlmutter

[11] Patent Number: 5,514,653
[45] Date of Patent: May 7, 1996

[54] METHOD OF BLOCKING THE SEC RECEPTOR

[75] Inventor: David H. Perlmutter, St. Louis, Mo.

[73] Assignee: Washington University, St. Louis, Mo.

[21] Appl. No.: 306,872

[22] Filed: Sep. 9, 1994

[51] Int. Cl.$^6$ ................................ A61K 38/16
[52] U.S. Cl. ............................. 514/12
[58] Field of Search .................. 530/324, 326; 514/12, 13; 435/7.21, 29, 240.1, 240.2

[56] References Cited

U.S. PATENT DOCUMENTS

| | | | |
|---|---|---|---|
| 5,137,873 | 8/1992 | Yankner | 514/2 |
| 5,157,019 | 10/1992 | Glover et al. | 514/12 |
| 5,164,295 | 11/1992 | Kisilevsky et al. | 435/7.92 |
| 5,175,253 | 12/1992 | Fallon et al. | 530/330 |
| 5,187,153 | 2/1993 | Cordell et al. | 514/2 |

OTHER PUBLICATIONS

J. Clin. Invest., vol. 90, issued Sep. 1992, Joslin et al, "The Serpin–Enzyme Complex (SEC) Receptor . . . ", pp. 1150–1154.

Brain Research, vol. 651, issued 1994, Khalil et al, "BA$_4$ 25–35 Modulates Substance P . . . ", pp. 227–235.

Perlmutter et al., Proc. Natl. Acad. Sci. USA 87, 3753–3737 (1990).

Perlmutter et al., J. Biol. Chem. 265, 16713–16716 (1990).

Joslin et al., J. Biol. Chem. 266, 21897–21902 (1991).

Yanker et al., Science 250, 279–282 (1990).

Joslin et al., J. Biol. Chem. 266, 11282–11288 (1991).

Yanker et al., N. Engl. J. Med. 325, 1849–1857 (1991).

Shearman et al., Proc. Natl. Acad. Sci. 91, 1470–1474 (1994).

Hansen et al., J. Immunol. Meth. 119, 203–210 (1989).

*Primary Examiner*—Jeffrey E. Russel
*Attorney, Agent, or Firm*—Scott J. Meyer

[57] ABSTRACT

A method is disclosed for blocking the SEC receptor and also inhibiting the neurotoxic effects of amyloid-β protein by treating SEC receptor-bearing cells with a synthetic inhibitor peptide, e.g. peptide PB145.

8 Claims, 5 Drawing Sheets

α$_1$AT Partial Amino Acid Seq.

```
PB446  Met Ser Ile Pro Pro Glu Val Lys Phe Asn Lys Pro Phe Val Phe Leu Met Ile Glu Gln
       1               5               10              15                  20
       Asn Thr Lys Ser Pro Leu Phe Met Gly Lys Val Val Asn Pro Thr Gln Lys [SEQ ID NO: 5]
                       25                  30                  35

PB96   Val Lys Phe Asn Lys Pro Phe Val Phe Leu Met Ile Glu Gln Asn Thr Lys Ser Pro Leu
       1               5               10              15                  20
       Phe Met Gly Lys Val Val Asn Pro Thr Gln Lys [SEQ ID NO: 6]
                       25                  30

PB154  Ile Glu Gln Asn Thr Lys Ser Pro Leu Phe Met Gly Lys Val Val Asn Pro Thr Gln Lys
       1               5               10              15                  20
       [SEQ ID NO: 7]
```

METHOD OF BLOCKING THE SEC RECEPTOR

BACKGROUND OF THE INVENTION

The present invention relates to a method of blocking the SEC receptor and also inhibiting neurotoxicity caused by amyloid-β protein, a peptide that has been implicated in Alzheimer's disease and is known to bind to the SEC receptor. More particularly, the invention relates to inhibiting the neurotoxic effects of amyloid-β protein with a synthetic peptide that blocks the SEC receptor. Note: Literature references on the following background information and on conventional test methods and laboratory procedures well known to the ordinary person skilled in the art and other such state-of-the-art techniques as used herein are indicated in parentheses and appended at the end of the specification, i.e. (1) to (21).

The serpin-enzyme complex (SEC) receptor recognizes a highly conserved domain in the carboxyl-terminal fragment of $α_1$-anti-trypsin (α1-AT) and several other serpins (1). The SEC receptor-binding domain of the serpins is only available for receptor recognition after the serpin has undergone a structural rearrangement. For instance, the SEC receptor recognizes serpins after they have formed a covalently-stabilized, inhibitory complex with a cognate serine-type enzyme. The SEC receptor also recognizes serpins which have been proteolytically modified by action of metalloenzymes or, in the case of α1-AT, by the collaborative action of reactive oxygen intermediates and serine-type enzymes. The SEC receptor was originally discovered because it mediated an increase in synthesis of α1-AT in response to α1-AT-elastase complexes. Thus, this receptor was shown to be involved in a feed-forward servomechanism which allows for inhibition of the enzymatic activity and, in turn, signalling to the cell to make more inhibitor. Presumably this prevents extensive destruction of surrounding tissue during the migration of phagocytes or the sprouting of cell processes as well as during wound repair. The SEC receptor has since been shown to mediate chemotaxis of neutrophils in response to serpin-enzyme complexes (2). The SEC receptor also internalizes its ligand by classical receptor-mediated endocytosis and delivers the ligand to an acidic compartment, probably lysosome, for intracellular degradation (3). Because its ligand specificity is similar to that for in vivo clearance/catabolism of serpin-enzyme complexes, it is also probably involved in in vivo clearance/catabolism of these complexes. Photoaffinity cross-linking studies and ligand-affinity chromatographic purification studies have shown that the receptor has an ~80 kDa ligand binding subunit (4). It is expressed in many cell types including hepatocytes, mononuclear phagocytes, neutrophils, epithelial cells, fibroblasts and cells of neuronal origin.

One interesting aspect of this receptor became apparent when the SEC receptor-binding domain of α1-AT was mapped in fine detail. A pentapeptide neodomain in the carboxyl terminal fragment of α1-AT was found to be sufficient for binding to the SEC receptor (5). See also U.S. Pat. No. 5,175,253. The interaction between the pentapeptide and the receptor was specific for length and sequence as shown by studies with deletions, substitutions and scrambling. The pentapeptide is a highly conserved region among the serpin family, thus explaining cross-competition for binding to the SEC receptor by several serpin-enzyme complexes, including α1-ACT-cat G, ATIII-thrombin, HCII-thrombin and, to a lesser extent, C1 inhibitor-C1s and PAI 1-TPA. This pentapeptide was also identified in the tachykinins and there was a similar sequence within the amyloid-β which had been implicated in toxic effects on neurons(6).

Amyloid-β is a major proteinaceous constituent of the extracellular deposits found in Alzheimer's disease (AD), and Down Syndrome (7). Most of the evidence suggests that amyloid-β is generated by abnormal proteolytic processing of the amyloid precursor protein (APP), which leads to extracellular deposition and represents the primary pathophysiologic element of these conditions. Several recent studies have implicated a neurotoxic effect for amyloid-β (6) or cores of amyloid plaques (8) by administration to cultured neurons or by injection into the brains of experimental animals. In one series of studies these effects were attributed to amyloid-β 25-35 and were blocked by substance P (6). In other studies, amyloid-β 25-35 was shown to enhance the neurotoxicity of glutamate (9-10). This effect of amyloid-β was elicited at a half-maximal concentration of ~40 nM and was not elicited by a peptide in which the sequence of the peptide had been reversed.

Because interaction of peptide ligands with the SEC receptor is half-maximally saturated at 40-50 nM and is sequence-specific, and because the SEC receptor is expressed on cells of neuronal origin (PC12), it constitutes an excellent candidate for mediating the neurotoxic effect of amyloid-β. Therefore, it was of some interest to the present inventor and colleagues to examine the possibility that the amyloid-β could bind to the SEC receptor. It has now been shown that amyloid-β, substance P and several other tachykinins bind to the SEC receptor (4). Amyloid-β, serpin-enzyme complexes, and peptide ligands for the SEC receptor do not bind to the substance P receptor. The SEC receptor is clearly distinct from the substance P receptor by several criteria:

First, the SEC receptor binds its ligands at a significantly lower affinity ($K_d$=50 nM vs 1 nM) and is expressed in greater number of plasma membrane molecules per receptor-bearing cell (~450,000 vs. 10,000-20,000).

Second, the SEC receptor is much less restricted in the specificity with which it recognizes ligand as compared to the substance P receptor. The SEC receptor recognizes peptide 105Y, substance P, substance K, and neurokinin B with approximately similar affinities, whereas the substance P receptor recognizes substance P with an affinity that is 2-3 orders of magnitude higher than that for substance K or neurokinin B. Moreover, the substance P receptor does not recognize peptide 105Y, α1-AT-protease complexes, bombesin, or amyloid-β. These two lines of evidence also make it likely that the SEC receptor is distinct from the substance K receptor and the neurokinin B receptor. The SEC receptor also recognizes its peptide ligands equally well with or without a C-terminal carboxyl-amide whereas the tachykinin receptors are markedly restricted in favor of a C-terminal carboxyl-amide.

A third line of evidence demonstrating the distinction between the SEC receptor and the substance P receptor is the absence of substance P receptor gene expression in HepG2 cells and human liver, known sites of expression of the SEC receptor. Thus, the SEC receptor, rather than the substance P receptor or other tachykinin receptors, is a prime candidate for mediating the neurotrophic/neurotoxic effects of amyloid-β.

Because data had shown that the SEC receptor mediated the neutrophil chemotactic effect of α1-AT-elastase complexes, it was predicted that amyloid-β and substance P would have neutrophil chemotactic effects. This prediction was shown to be correct (2). Even more importantly, studies of the neutrophil chemotactic effects of these peptides showed that substance P elicited homologous desensitization of the SEC receptor on neutrophils to the chemotactic effects of amyloid-β. Desensitization of the SEC receptor by substance P is, therefore, a possible explanation for the previous observation that substance P inhibits the trophic/toxic effects of amyloid-β on neurons (6).

In recent studies, the present inventor and colleagues have examined the possibility that the SEC receptor is expressed on cells of neuronal origin. The results confirm the original observation that the NGF-responsive, ganglionic cell line PC12 bears abundant SEC receptor. In addition, expression of the SEC receptor has been demonstrated in the human glioblastoma lines U138MG and U373MG and in the human astrocytoma cell line STTG-1.

In addition to the findings which suggest that the SEC receptor mediates trophic/toxic effects on neurons, there are several other possible ways in which the SEC receptor may be involved in the secondary pathophysiological events that lead to dementia in AD:

First, it is possible that the SEC receptor plays a role in the local inflammatory response associated with amyloid-β deposition. Although it has not been emphasized in the description of AD, several studies have reported an inflammatory response surrounding amyloid plaques. In studies of immune-associated antigens in human post-mortem samples, several reports show that expression of HLA-DR major histocompatibility antigen on microglial cells adjacent to amyloid plaques (11). Moreover, microglial cell proliferation and scavenging activity as well as T cell infiltration was reported at plaque sites (12). Because the SEC receptor has been demonstrated on the surfaces of cells of myeloid lineage, including monocytes and neutrophils, and because the SEC receptor has been demonstrated on the surface of human glioblastoma cell lines, as described above, it is possible that it is expressed on microgila in vivo. Moreover, it becomes a formal possibility that interaction of a ligand such as amyloid-β with the SEC receptor plays a role in the directed migration of microgila, as it does for neutrophils, or in the expression of pro-inflammatory and/or anti-inflammatory products by microglia. Several studies have indicated that molecules which are known ligands for the SEC receptor elicit production of pro-inflammatory and anti-inflammatory cytokines. Kurdowska and Travis showed that α1-antichymotrypsin-protease complexes and proteolytically modified α1-antichymotrypsin mediated an increase in production of IL-6 by fibroblasts (13). Although it has not yet been studied formally, this effect is likely to be mediated by the SEC receptor. α1-antichymotrypsin-catG complexes and proteolytically modified α1-ACT cross-compete for binding of α1-AT-elastase complexes to HepG2 cells (14), and desensitize neutrophils to the chemotactic effect of α1-AT-elastase complexes (15).

Tilg et al have recently shown that peptide 105C (pentapeptide which binds to the SEC receptor), but not peptide 105C—C (tetrapeptide with deletion of C-terminal amino acid of peptide 105C, which does not bind to the SEC receptor) mediates induction of interleukin-1 receptor antagonist (IL-1RA) and interleukin-1 (IL-1β) in peripheral blood mononuclear cells, with 5-to 10-fold greater induction of IL-1RA than IL-1β (16). IL-1RA is known to block the biological activity of IL-1β (17). This may be particularly important in AD in that IL-1β has been shown to mediate increases in synthesis of the amyloid precursor protein (18), and therein, could increase the tendency toward amyloid-β deposition in a susceptible genetic background.

Second, the SEC receptor may mediate ingrowth of neurites into the amyloid plaques. The SEC receptor is expressed on PC12 neuronal cells and is capable of mediating directed migration of cells such as neutrophils. An effect of this type on neurons is very important since ingrowth and degeneration of neurites is considered one of the hallmarks distinguishing mature plaques, associated with dementia, and diffuse plaques, associates with aging.

Taken together, these considerations suggest that the SEC receptor plays a role in this pathophysiology of pre-senile dementia associated with AD and that pharmacologic blockage of this receptor can be used to prevent formation of mature plaques, and, in turn, neuronal degeneration and dementia.

Although scientific explanation of the role of the SEC receptor is described herein, it is to be understood that the inventor is not limited to any particular scientific theory.

BRIEF DESCRIPTION OF THE INVENTION

In accordance with the present invention, a method is provided for blocking the SEC receptor and also inhibiting the neurotoxic effects of amyloid-β protein. The method comprises treatment of SEC receptor bearing cells with a synethetic peptide that blocks the SEC receptor. A preferred such inhibitor is a peptide designated PB145, which is described in U.S. Pat. No. 5,157,019. Peptide PB145 is a 43mer having the following amino acid sequence:

Ile—Ala—Gly—Arg—Ser—Leu—Asn—Pro—Asn—Arg—Val—Thr—
　　　　　　　　　5　　　　　　　　　　　　　10

Leu—Arg—Tyr—Asn—Lys—Pro—Phe—Ile—Leu—Val—Leu—Phe—
　　　　　15　　　　　　　　　　　　　　20

Glu—Thr—Pro—Gly—Asn—Ser—Leu—Val—Phe—Leu—Gly—Arg—
25　　　　　　　　　　　　　30　　　　　　　　　　　　　35

Ile—Ser—Asn—Pro—Ala—Thr—Lys   [SEQ ID NO:1]
　　　　　　　　40

The effects of the pathogenic role of amyloid-β protein have been localized to a discrete 11-amino acid internal sequence designated amyloid-β 25–35 and having the following amino acid sequence (6):

Gly—Ser—Asn—Lys—Gly—Ala—Ile—Ile—Gly—Leu—Met   [SEQ ID NO:2]
　　　　　　5　　　　　　　　　　　　10

The inhibitory effect of peptide PB145 on the amyloid-β 25–35-mediated neurotoxicity is shown herein to be concentration-dependent. The effect is evident at concentrations as low as 0.33 μM. The toxicity of amyloid-β 25–35 to the human glio-blastoma cell line U373MG also is shown herein to be completely inhibited by peptide PB145. Since amyloid-β 25–35 is a primary constituent of senile plaques and cerebrovascular deposits in Alzheimer's disease and Down Syndrome, inhibition of the neurotoxic effects of that peptide indicates additional usefulness of PB145 in diagnosis and treatment of these diseases.

Other useful synthetic peptides that block the SEC receptor are peptides PB446 and PB96, which are fragments of the $\alpha_1$-antitrypsin carboxy terminal sequence. PB90 is a 31mer having the following amino acid sequence:

Val—Lys—Phe—Asn—Lys—Pro—Phe—Val—Phe—Leu—Met—Ile—
                   5                          10

Glu—Gln—Asn—Thr—Lys—Ser—Pro—Leu—Phe—Met—Gly—Lys—
           15                    20

Val—Val—Asn—Pro—Thr—Gln—Lys   [SEQ ID NO:3]
25                    30

PB446 is a 37mer having the following amino acid sequence:

Met—Ser—Ile—Pro—Pro—Glu—Val—Lys—Phe—Asn—
            5                   10

Lys—Pro—Phe—Val—Phe—Leu—Met—Ile—Glu—Gln—
           15                 20

Asn—Thr—Lys—Ser—Pro—Leu—Phe—Met—Gly—Lys—
           25                 30

Val—Val—Asn—Pro—Thr—Gln—Lys   [SEQ ID NO:5]
             35

Although specific peptides are described herein, it will be appreciated that analogous peptides that block the SEC receptor are included within the scope of the invention. Such peptides are, for example, peptide fragments which overlap the SEC receptor-binding domain and are relatively resistant to degradation or have other properties related to those of PB 145. Variations in the constituent amino acids and/or the addition or removal of amino acids in the peptide chain which do not adversely or detrimentally affect the biologic activity of the peptide as defined herein are included within the scope of the invention. It should also be understood that the inhibitory activity of PB 145 may be due in part to blocking of the SEC receptor and in part to providing an alternate binding site for amyloid-β peptide. Thus, it should be understood that the invention is not limited to any particular scientific theory.

DETAILED DESCRIPTION OF THE INVENTION

NOTE: WHILE THE SPECIFICATION CONCLUDES WITH CLAIMS PARTICULARLY POINTING OUT AND DISTINCTLY CLAIMING THE SUBJECT MATTER REGARDED AS FORMING THE PRESENT INVENTION, IT IS BELIEVED THAT THE INVENTION WILL BE BETTER UNDERSTOOD FROM THE FOLLOWING PREFERRED EMBODIMENTS OF THE INVENTION TAKEN IN CONNECTION WITH THE ACCOMPANYING DRAWINGS:

In order to illustrate the invention in greater detail, the following specific laboratory examples were carried out (although specific examples and details are thus illustrated herein, it will be appreciated that the invention is not limited to these specific examples or details):

EXAMPLES

The MTT assay (19) was used to monitor the neurotoxicity of amyloid-β peptide. This assay has been shown to correlate with the LDH assay and morphologic changes of neurotoxicity in the neuronal cell line PC 12 and in cortical neurons in primary culture (20,21). Inhibition of MTT reduction is a specific, early indicator of amyloid-β-mediated cytotoxicity. The PC12 cell line was used because it is the most well characterized cell line of neuronal origin and because previous studies have shown there is abundant expression of SEC receptor in this cell line. Using $^{125}$I peptide 105Y there is specific, saturable binding. Scatchard plot analysis predicts a $K_d$~34.3 nM and ~180,000 plasma membrane receptors per cell.

Figure 1:
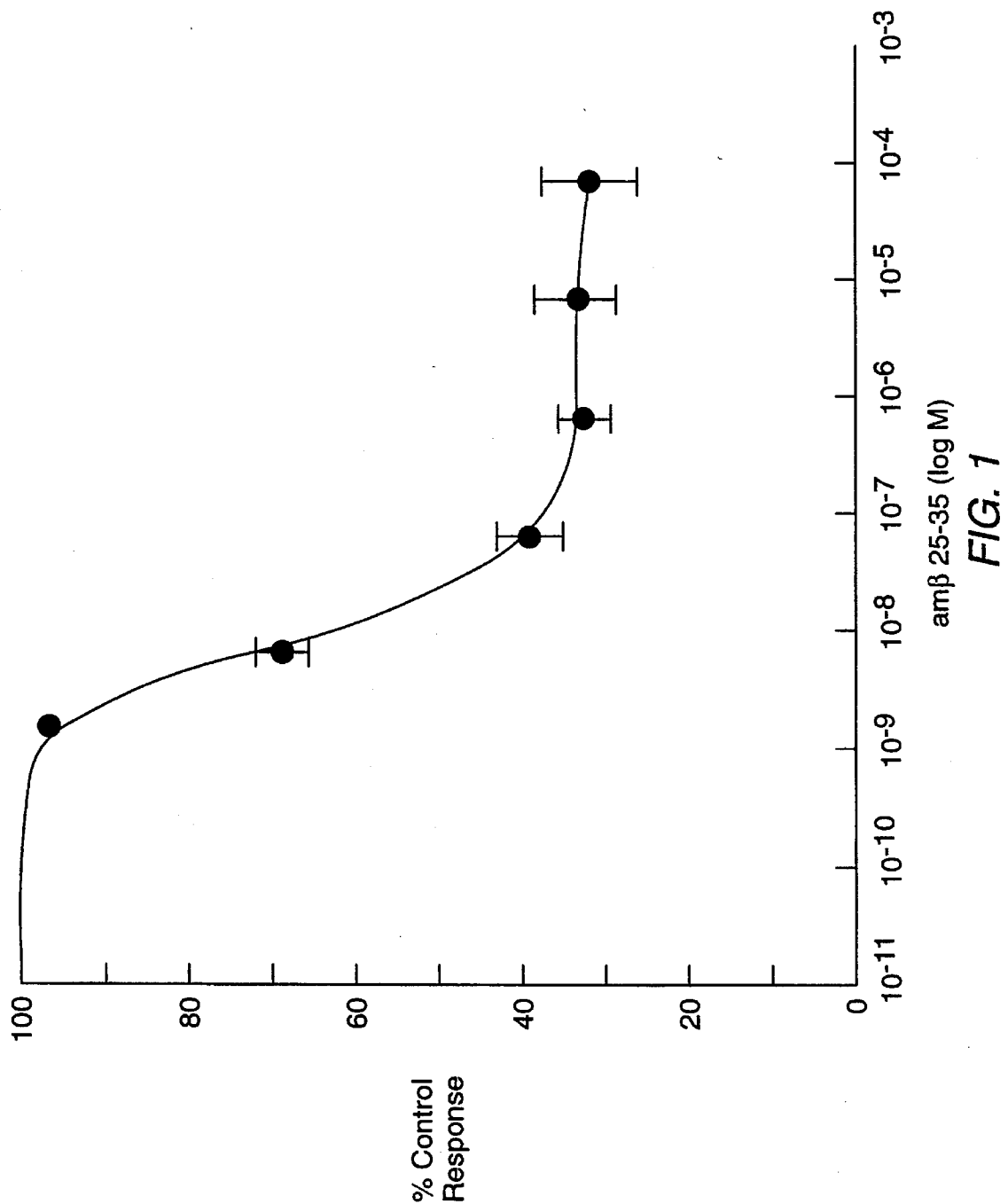
FIG. 1 is a graphical representation which shows the effect of amyloid-β 25–35 on MTT reduction in PC12 cells. The reduction in percent control response is plotted on the y-axis against the concentration (logM) of the amyloid-β 25–35 on the x-axis.

First, the effect of amyloid-β 25–35 on MTT reduction in PC12 cells was examined (FIG. 1). PC12 cells were incubated for six (6) hours at 37° C. with amyloid-β 25–35 in several different concentrations as shown on the horizontal axis. MTT was added and the cells incubated at 37° C with amyloid-β 25–35 in several different concentrations as shown on the horizontal axis. MTT was added and the cells incubated at 37° C. for another two (2) hours. Cell extraction buffer was added and the incubation continued at 37° C. overnight. Cell extracts were then subjected to spectrophotometric analysis at 570 nm. Results were reported as percent control response as determined by the difference between control cells and cells lysed prior to incubation with MTT. The results show a concentration-dependent decrease in MTT reduction in response to amyloid-β 25–35. The point of half-maximal reduction is between $10^{-9}$ to $10^{-8}$ M which correlates well with the point of half-maximal saturation of the SEC receptor.

Figure 2:
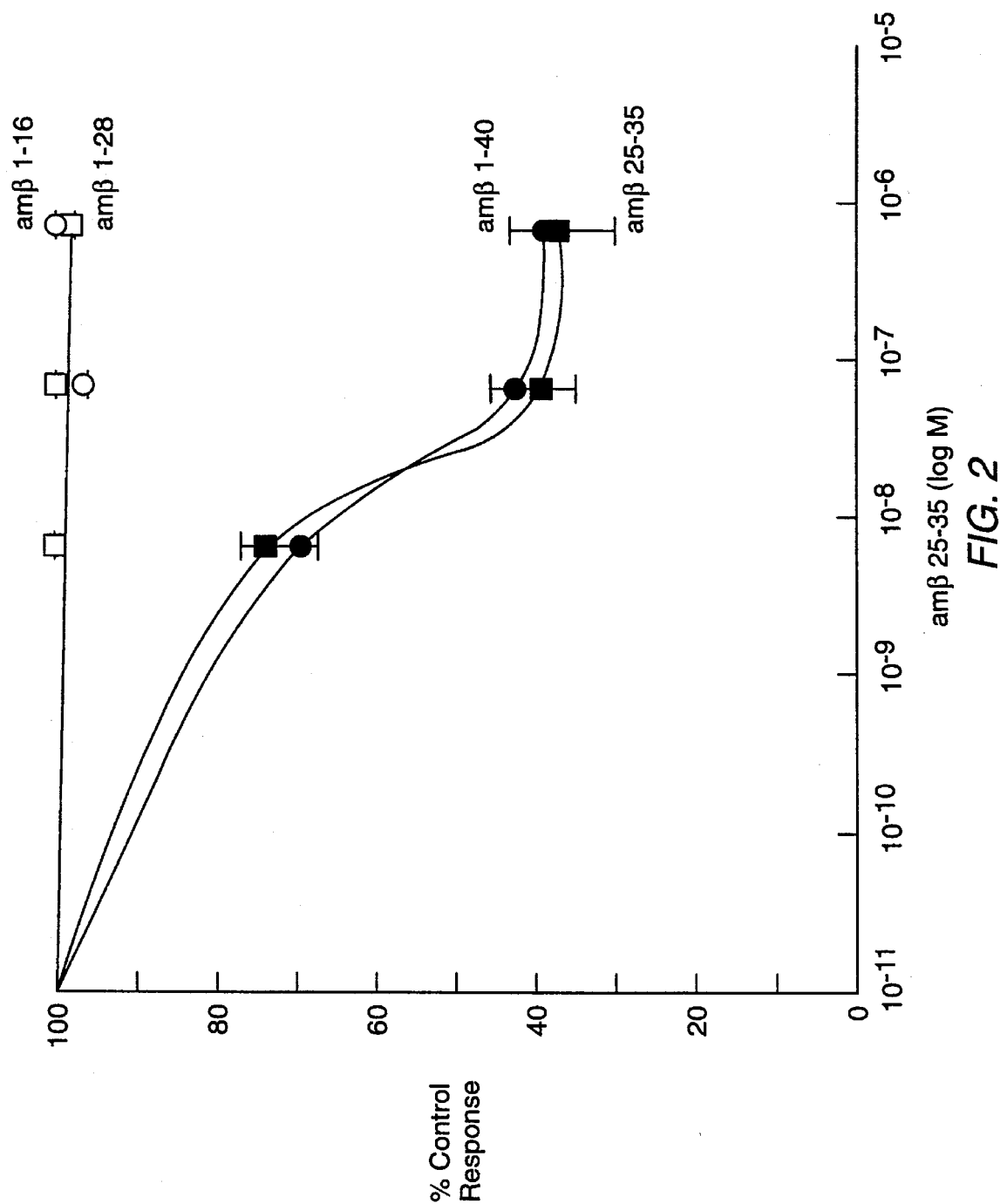
FIG. 2 is a graphical representation of the effect of amyloid-β 25–35 as shown in FIG. 1 in comparison to corresponding effect of other regions of the amyloid-β protein, namely amyloid-β 1–40, amyloid-β 1–16 and amyloid-β 1–28 in PC12 cells.

Second, the specificity of the effect of amyloid-β 25–35 on MTT reduction in PC12 cells was examined (FIG. 2). The results show that amyloid-β 1–40 has an effect similar to that of amyloid-β 25–35, but amyloid-β 1–16 and amyloid-β 1–28 have no effect. These data indicate that the effect is specific for the region corresponding to amyloid-β 25–35.

Figure 3:
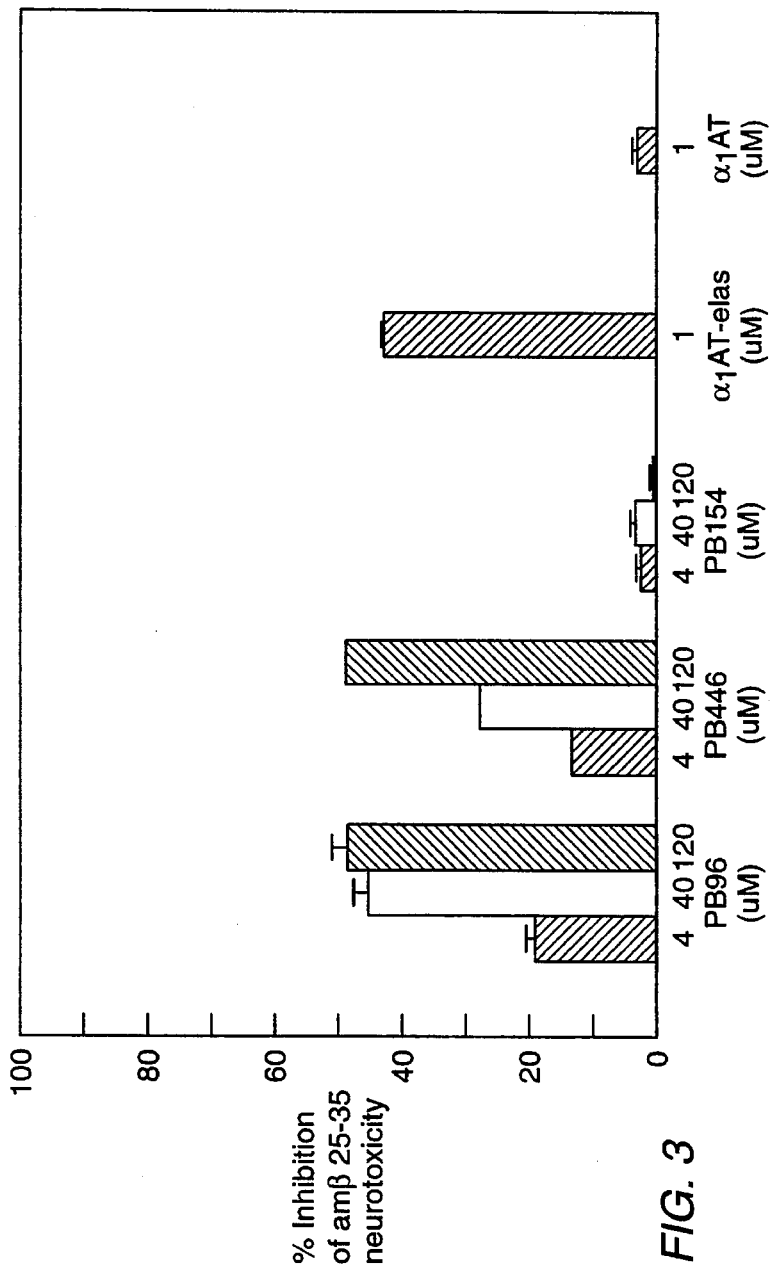
FIG. 3 is a bar graph which shows the percent inhibition of amyloid-β 25–35 neurotoxicity in the absence or presence of various peptides, namely peptide PB 96, peptide PB 446, control peptide PB 154, $\alpha_1$-antitrypsin-elastase ($\alpha_1$-AT-elas) and $\alpha_1$-AT at various concentrations (μM) in PC12 cells. The amino acid sequences of PB 96, PB 446 and PB 96 relative to the partial sequence of $\alpha_1$-AT of which they are fragments are shown at the top of the bar graph.

Third, the possibility that the effect of amyloid-β 25–35 is mediated by the SEC receptor was examined (FIG. 3). In this case PC12 cells were incubated with amyloid-β 25–35 in the absence or presence of peptide 96 or peptide 446 which compete for binding to the SEC receptor. Peptides 96 and 446 inhibit the effect of amyloid-β 25–35, but negative control peptide 154 does not. PC12 cells were also incubated with $\alpha_1$-AT-elastase complexes which compete for binding to the SEC receptor. $\alpha_1$-AT-elastase complexes inhibit the effect of amyloid-β 25–35, but negative control native α1-AT does not. These data suggest that the effect of amyloid-β 25–35 is mediated by the SEC receptor. However, for each of these peptides the effect is short-term and each has weak agonistic activity at high concentrations when used alone.

Figure 4:
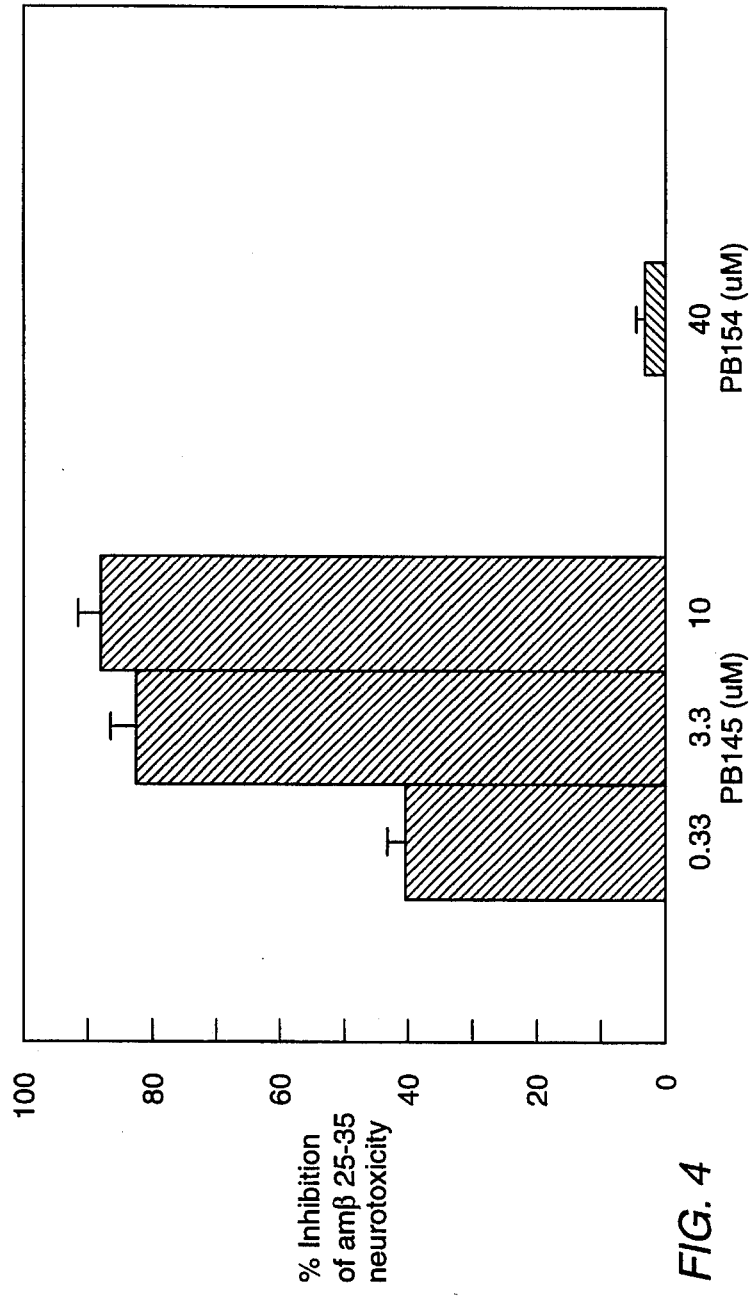
FIG. 4 is a bar graph which shows the percent inhibition of amyloid-β 25–35 neurotoxicity in the presence of peptide PB145 or control peptide PB 154 at various concentrations (μM) in PC12 cells. The amino acid sequences of these two peptides compared to the partial sequence of $\alpha_1$-AT are shown at the top of the bar graph.

Fourth, the possibility that peptide PB145 inhibits the toxic effect of amyloid-β 25–35 was examined (FIG. 4). The effect is concentration-dependent. The effect is evident at concentrations as low as 0.33 μM. The effect is time-dependent, but lasts at least 24 hours. Peptide PB145 did not have any neurotoxic activity by itself.

Figure 5:
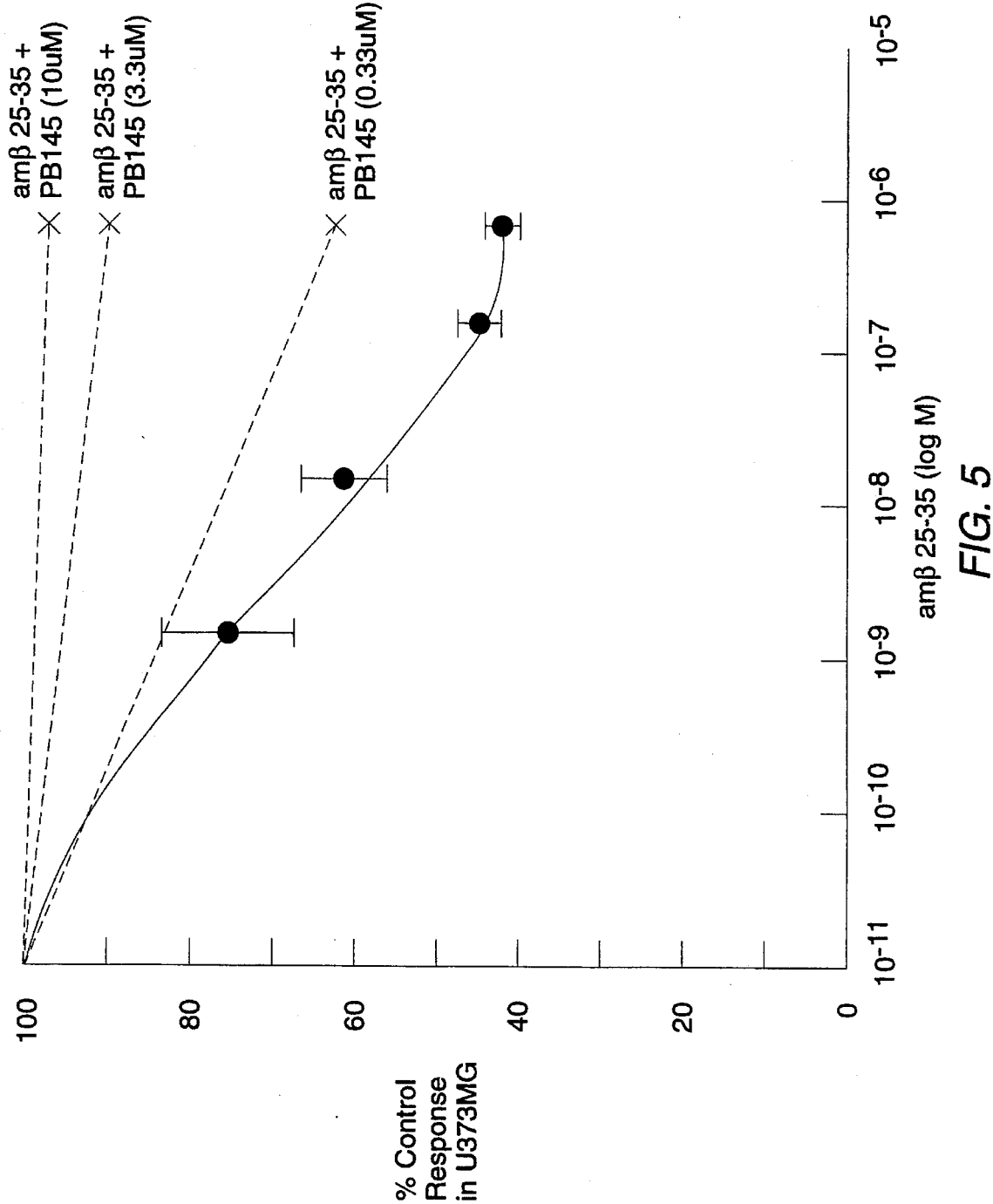
FIG. 5 is a graphical representation which shows the toxic effect of amyloid-β 25–35 on other SEC receptor-bearing cell types in U373MG cells and the inhibition of neurotoxicity in the presence of peptide PB145. The reduction in percent control is plotted on the y-axis against the concentration (logM) of the amyloid-β 25–35 on the x-axis.

Fifth, the possibility that amyloid-β 25–35 is toxic to other SEC receptor-bearing cell types and that PB145 inhibits its toxic effects in these other cell types was examined (FIG.5). In this case a human glioblastoma cell line U373MG was used. The results show that amyloid-β 25–35 is also toxic to the U373MG cell line, and that its toxicity is completely inhibited by PB145.

The neuronal cell line PC12 and the human glioblastoma cell line U373MG used in the assays described herein are conventional cell lines well known to the person skilled in the art and readily available to the public. For example, both cell lines are available to the public from the American Type Culture Collection, Rockville, Md., under accession numbers ATCC CRL 1721 (for PC12) and ATCC HTB 17 (for U373MG).

In the MTT assay used herein, inhibition of cellular redox activity is measured by 3-[4,5-dimethylthiazol-2-yl]-2,5-diphenyltetrazolium bromide (MTT) by conventional procedures as described by Hansen et al. (19).

Various other examples will be apparent to the person skilled in the art after reading the present disclosure without departing from the spirit and scope of the invention. It is intended that all such other examples be included within the scope of the appended claims.

References

1. Perlmutter D. H., Glover G. I., Rivetna M., Schasteen C. S., Fallon R. J. Identification of a serpin-enzyme complex (SEC) receptor on human hepatoma cells and human monocytes. *Proc Natl Aced Sci USA* 1990; 87:3753–3737.

2. Joslin G., Griffin G. L., August A. M., Adams S., Fallon R. J., Senior R. M., Perlmutter D. H. The serpin-enzyme complex (SEC) receptor mediates the neutrophil chemotactic effect of α1-antitrypsin-elastase complexes and amyloid-β peptide. *J Clin Invest* 1992; 90:1150–1154.

3. Perlmutter D. H., Joslin G., Nelson P., Schasteen C., Adams S. P. Fallon R. J. Endocytosis and degradation of α1-antitrypsin-protease complexes is mediated by the SEC receptor. *J Biol Chem* 1990; 165:16713–16716.

4. Joslin G., Krause J. E., Hershey A. D., Adams S. P., Fallon R. J., Perlmutter D. H. Amyloid-β peptide, substance P and bombesin bind to the serpin-enzyme (SEC) receptor. *J Biol Chem* 1991; 266:21897–21902.

5. Joslin G., Fallon R. J., Bullock J., Adams S. P., Perlmutter D. H. The SEC receptor recognizes a pentapeptide neo-domain of α1-antitrypsin-protease complexes. *J Biol Chem* 1991; 266:11281–11288.

6, Yanker B. A., Duffy L. K., Kirschner D. A. Neurotrophic and neurotoxic effects of amyloid-β protein: reversal by tachykinin neuropeptides. *Science* 1990; 250:279–282.

7. Selkoe D. J. Amyloid-β protein precursor and the pathogenesis of Alzheimer's disease. *Cell* 1989; 58:611–612.

8. Frautschy S. A., Baird A., Cole G. M. Effects of Injected Alzheimer β-amyloid cores in rat brain. *Proc Natl Acad Sci* USA 1091; 88:8362–8366.

9. Koh J-Y., Yang L. L., Cotman C. W. β-amyloid protein increases the vulnerability of cultured cortical neurons to excitotoxic damage. *Brain Res* 1990; 533:315–320.

10. Mattson M. P., Cheng B., David D., Bryant K., Lieberburg I., Rydel R. E. β-Amyloid peptides destabilized calcium homeostasis and render human cortical neurons vulnerable to excitotoxicity. *J Neurosic* 1992; 12:378–389.

11. Itagaki S., McGeer P. I., Akiyama H., Zhu S., Selkoe D. Relationship of microgila and astrocytes to amyloid deposits of Alzheimer's disease. *J Neuroimmunology* 1989: 24:173–182.

12. Rogers J., Luber-Narod J., Styren S. D., Civin W. H. Expression of Immune system-associated antigens by cells of the human central nervous system: relationship to the pathology of Alzheimer's disease. *Neurobiol Aging* 1988; 9:339–349.

13. Kurdowska A., Travis J. Acute phase protein stimulation by α1-antichymotrypsin-cathepsin G complexes: Evidence for the Involvement of interleukin-6. *J Biol Chem* 1990; 265:21023–21026.

14. Joslin G., Witwer A., Adams S. P., Tollefsen D. M., August A. M., Perlmutter D. H. Cross competition for binding of α1-antitrypsin (α1-AT)-elastase complexes to the SEC receptor by other serpin-enzyme complexes and by proteolytically modified α1-AT. *J Biol Chem* 1993; 268:1886–1893.

15. Potempa J., Fedak O., Dubin A., Mast A., Travis J. Proteolytic Inactivation of α1-antichymotrypsin. Site of cleavage and generation of chemotactic activity. *J Biol Chem* 1991; 266:21482–21487.

16. Tilg H., Vannier E., Vachino G., Dinarello C. A., Mier J. W. Anti Inflammatory properties of hepatic acute phase proteins: Preferential Induction of interleukin I (IL-1) receptor antagonist over IL-1β synthesis by human peripheral blood mononuclear cells. *J Exp Med* 1991; 178:1629–1636.

17. Arend W. P. Interleukin 1 receptor antagonist: A new member of the interleukin 1 family. *J Clin Invest* 1991; 88:1445–1451.

18. Goldgaber D., Harris H. W., Hia T., Maciag T., Donnelly R. J., Jacobsen J. S., Vilek M. P., Gajdusek D. C. Interleukin 1 regulates synthesis of amyloid-β protein precursor mRNA in human endothelial cells. *Proc Natl Acad Sci USA* 1989; 86:7606–7610.

19. Hansen M. B., Nielsen S. E., Burg K. Re-examination and further development of a precise and rapid dye method for measuring cell growth/cell kill. *J Immunol Meth* 1989; 119:203–210.

20. Shearman M. S., Ragan C. I., Iversen L. L. Inhibition of PC12 cell radox activity is a specific, early indicator of the mechanism of β-amyloid-mediated cell death. *Proc Natl Acad Sci USA* 1994; 91:1470–1474.

21. Behl C., Davis J. B., Lesley R., Schubert D. Hydrogen peroxide mediates amyloid-β protein toxicity. *Cell* 1994; 77:817–827.

What is claimed:

1. A method of blocking the SEC receptor which comprises subjecting SEC receptor-bearing cells to an inhibitorily effective amount of a peptide selected from the group consisting of PB145, PB96 and PB446.

2. The method of claim 1 in which the SEC receptor-bearing cells are PC12 cells.

3. The method of claim 1 in which the peptide is PB145.

4. A method of inhibiting amyloid-β protein neurotoxicity which comprises subjecting SEC receptor-bearing cells to an inhibitorily effective amount of a peptide selected from the group consisting of PB145, PB96 and PB446.

5. The method of claim 4 in which the SEC receptor-bearing cells are PC12 cells or human glioblastoma cells U373MG.

6. The method of claim 4 in which the peptide is PB145.

7. A method for the treatment of Alzheimer's disease comprising administering to a host manifesting said disease an effective amount of a peptide selected from the group consisting of PB145, PB96 and PB446 for inhibiting amyloid-β neurotoxicity in said host.

8. The method of claim 7 in which the peptide is PB145.

* * * * *

UNITED STATES PATENT AND TRADEMARK OFFICE
CERTIFICATE OF CORRECTION

PATENT NO. : 5,514,653
DATED : MAY 7, 1996
INVENTOR(S) : DAVID H. PERLMUTTER

It is certified that error appears in the above-identified patent and that said Letters Patent is hereby corrected as shown below:

At Col. 5, Line 14, "PB90" should read
--PB96--.

Signed and Sealed this

Twenty-eighth Day of January, 1997

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 43 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Ile Ala Gly Arg Ser Leu Asn Pro Asn Arg Val Thr Leu Arg Tyr Asn
1               5                   10                  15

Lys Pro Phe Ile Leu Val Leu Phe Glu Thr Pro Gly Asn Ser Leu Val
            20                  25                  30

Phe Leu Gly Arg Ile Ser Asn Pro Ala Thr Lys
        35                  40
```

( 2 ) INFORMATION FOR SEQ ID NO:2:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Gly Ser Asn Lys Gly Ala Ile Ile Gly Leu Met
1               5                   10
```

( 2 ) INFORMATION FOR SEQ ID NO:3:

( i ) SEQUENCE CHARACTERISTICS:
( A ) LENGTH: 31 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Val Lys Phe Asn Lys Pro Phe Val Phe Leu Met Ile Glu Gln Asn Thr
1               5                   10                  15

Lys Ser Pro Leu Phe Met Gly Lys Val Val Asn Pro Thr Gln Lys
            20                  25                  30
```

( 2 ) INFORMATION FOR SEQ ID NO:4:

( i ) SEQUENCE CHARACTERISTICS:

(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO:4:

```
Ile Glu Gln Asn Thr Lys Ser Pro Leu Phe Met Gly Lys Val Val Asn
 1               5                  10                 15
Pro Thr Gln Lys
             20
```

(2) INFORMATION FOR SEQ ID NO:5:

(i) SEQUENCE CHARACTERISTICS:
(A) LENGTH: 37 amino acids
(B) TYPE: amino acid
(D) TOPOLOGY: linear (ii) MOLECULE TYPE: peptide (xi) SEQUENCE DESCRIPTION: SEQ ID NO:5:

```
Met Ser Ile Pro Pro Glu Val Lys Phe Asn Lys Pro Phe Val Phe Leu
 1               5                  10                 15
Met Ile Glu Gln Asn Thr Lys Ser Pro Leu Phe Met Gly Lys Val Val
                20                  25                 30
Asn Pro Thr Gln Lys
                35
```

(2) INFORMATION FOR SEQ ID NO:6:

(i) SEQUENCE CHARACTERISTICS:
(A) LENGTH: 31 amino acids
(B) TYPE: amino acid
(D) TOPOLOGY: linear (ii) MOLECULE TYPE: peptide (xi) SEQUENCE DESCRIPTION: SEQ ID NO:6:

```
Val Lys Phe Asn Lys Pro Phe Val Phe Leu Met Ile Glu Gln Asn Thr
 1               5                  10                 15
Lys Ser Pro Leu Phe Met Gly Lys Val Val Asn Pro Thr Gln Lys
                20                  25                 30
```

(2) INFORMATION FOR SEQ ID NO:7:

(i) SEQUENCE CHARACTERISTICS:
(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO:7:

```
Ile Glu Gln Asn Thr Lys Ser Pro Leu Phe Met Gly Lys Val Val Asn
 1               5                  10                 15
Pro Thr Gln Lys
             20
```

(2) INFORMATION FOR SEQ ID NO:8:

(i) SEQUENCE CHARACTERISTICS:
(A) LENGTH: 36 amino acids
(B) TYPE: amino acid
(D) TOPOLOGY: linear (ii) MOLECULE TYPE: peptide (xi) SEQUENCE DESCRIPTION: SEQ ID NO:8:

```
Ser Ile Pro Pro Glu Val Lys Phe Asn Lys Pro Phe Val Phe Leu Met
 1               5                  10                  15
Ile Glu Gln Asn Thr Lys Ser Pro Leu Phe Met Gly Lys Val Val Asn
                20                  25                  30
Pro Thr Gln Lys
            35
```